(12) United States Patent
Takata

(10) Patent No.: US 9,125,813 B2
(45) Date of Patent: Sep. 8, 2015

(54) PROCESS FOR PRODUCING GLUCOMANNAN GEL PARTICLES

(75) Inventor: Tadahiko Takata, Onomichi (JP)

(73) Assignee: SHIMIZU CHEMICAL CORPORATION, Hiroshima-Ken (JP)

( * ) Notice: Subject to any disclaimer, the term of this patent is extended or adjusted under 35 U.S.C. 154(b) by 2661 days.

(21) Appl. No.: 11/087,870

(22) Filed: Mar. 24, 2005

(65) Prior Publication Data

US 2006/0127557 A1 Jun. 15, 2006

(30) Foreign Application Priority Data

Dec. 14, 2004 (JP) ................................. 2004-360685

(51) Int. Cl.
| | |
|---|---|
| *A61K 35/12* | (2015.01) |
| *A61K 8/04* | (2006.01) |
| *A61K 8/73* | (2006.01) |
| *A61Q 5/02* | (2006.01) |
| *A61Q 11/00* | (2006.01) |
| *A61Q 19/10* | (2006.01) |
| *C08J 3/075* | (2006.01) |
| *C08J 3/14* | (2006.01) |

(52) U.S. Cl.
CPC ................ *A61K 8/044* (2013.01); *A61K 8/042* (2013.01); *A61K 8/73* (2013.01); *A61Q 5/02* (2013.01); *A61Q 11/00* (2013.01); *A61Q 19/10* (2013.01); *C08J 3/075* (2013.01); *C08J 3/14* (2013.01); *A61K 2800/28* (2013.01); *A61K 2800/412* (2013.01); *C08J 2305/14* (2013.01)

(58) Field of Classification Search
None
See application file for complete search history.

(56) References Cited

U.S. PATENT DOCUMENTS

| | | | |
|---|---|---|---|
| 3,856,945 A | 12/1974 | Sugiyama et al. | |
| 5,366,671 A | 11/1994 | Kimura | |
| 6,558,652 B2 * | 5/2003 | Takata | ........................... 424/49 |
| 6,586,590 B1 * | 7/2003 | Renn et al. | .................... 536/128 |

FOREIGN PATENT DOCUMENTS

| | | |
|---|---|---|
| JP | 06-321728 A | 11/1994 |
| JP | 11-032703 A | 2/1999 |

* cited by examiner

*Primary Examiner* — Snigdha Maewall
(74) *Attorney, Agent, or Firm* — Miller, White, Zelano, Branigan, P.C.

(57) ABSTRACT

A particulate glucomannan gel is produced by dissolving glucomannan-rich flour in water, precipitating glucomannan from the solution with ethanol, treating the precipitated glucomannan with an alkali to transform to water-insoluble, irreversible hydrogel particles, recovering and drying the hydrogel particles, and milling dried particles to a desired particle size. The resulting gel particles are incorporated into hygienic or cosmetic preparations as a deposit-cleaning agent.

18 Claims, No Drawings

PROCESS FOR PRODUCING GLUCOMANNAN GEL PARTICLES

BACKGROUND OF THE INVENTION

This invention relates to a process for producing glucomannan gel particles which are useful as a deposit-cleaning agent to be formulated into hygienic and cosmetic preparations.

As is well-known, dental pastes generally contain a particulate material such as calcium carbonate, calcium phosphate, calcium sulfate, aluminum hydroxide or silica for removing deposit from the tooth by a scrubbing or exfoliating effect. In order to minimize damages to the enamel and gingiva, synthetic polymer beads have also been used. A particulate material is also used in cosmetic preparations. JP-A-06033416 discloses a skin-cleansing preparation containing a cross-linked polymer bead having a certain degree of elasticity.

The known scrubbing agents are comprised of a hard particulate material which remains hard when incorporating into hygienic and cosmetic preparations. It would be desirable to have a particulate material which, in use in the hygienic or cosmetic preparation, has a relatively soft layer on at least surfaces thereof to minimize damages to the tissue to be cleaned while retaining physical properties as a whole sufficient to exhibit scrubbing or exfoliating effects.

Applicant has disclosed in JP 2000-344801A and U.S. Pat. No. 6,558,652 a process for producing glucomannan particles which are useful as a deposit-cleaning agent to be formulated into hygienic and cosmetic preparations. The process comprises the steps of adding a glucomannan-rich flour to an aqueous ethanol containing about 40 to 50% of ethanol, allowing the flour particles to swell in the aqueous ethanol, treating the swollen flour particles with an alkali to form gelled flour particles, separating the gelled flour particles from the liquid; and drying the gelled particles. The resulting gel particles are hard and insoluble in water but swell with water to form a soft skin layer surrounding a hard core portion.

It has been found that this process suffers from certain disadvantages. First, the particle size of the resulting gel particles depends on the particle size of the starting glucomannan-rich flour and not controllable arbitrarily to a particle size suitable for particular applications. Second, excessive swelling of the starting flour may cause the dried gel particles to be completely swellable with water to form soft swollen particles free from hard core portions.

A need exists for providing a process for producing glucomannan particles which can eliminate or ameliorate the above disadvantages.

SUMMARY OF THE INVENTION

The above need may be met by the present invention. According to the present invention, there is provided a process for producing a particulate glucomannan gel comprising the steps of:

a) dissolving a glucomannan-rich flour in water to make a solution;

b) mixing the resulting solution with ethanol to precipitate glucomannan;

c) adding an alkali to the resulting mixture to transform the precipitated glucomannan into water-insoluble, irreversible hydrogel particles;

d) separating the glucomannan hydrogel particles from the liquid;

e) drying the separated hydrogel particles; and f) milling the dried gel particles to a desired particle size.

The above process enables the particle size of the final product to be controlled independently from that of the starting glucomannan flour. The particulate glucomannan gel produced by the process according to the present invention is particularly suitable for use in hygienic and cosmetic preparations as a deposit-scrubbing or exfoliating agent. The dried gel particles can absorb only a limited amount of water such that at least surface portions thereof transform from a glassy state to a rubbery state without reverting to the hydrogel before drying. Accordingly, the dried glucomannan particles formulated in hygienic or cosmetic preparations can minimize damages to the tissue to be cleaned and also afford a pleasant massage effect when rolling on the skin.

DETAILED DISCUSSION

Glucomannan is a polysaccharide complex found in the tuber of *Amorphophallus* species such as *A. konjac*. Aqueous solutions of glucomannan in the form of a hydrosol produce a water-insoluble, thermally irreversible hydrogel when reacting the sol with an alkali. This process has long been utilized in Japan, China and other countries for the production of a foodstuff called "*konjac*" from *Amorphophallus* tuber flour called "*konjac* flour".

Any glucomannan-rich flour derived from tubers of an *Amorphophallus* species, typically *A. konjac* may be employed. Purified glucomannan flour and refined *konjac* flour are preferred. Crude glucomannan-containing flour commonly referred to as "*konjac* flour" is a product obtained by slicing, drying and grinding whole tubers of an *Amorphophallus* species, typically *A. konjac* to a particle size of 0.5 mm or less. Refined *konjac* flour is produced by pneumatically classifying the crude *konjac* flour to remove starch or other impurities and has a carbohydrate content of about 80% or higher by weight. Purified glucomannan flour are produced from crude or refined *konjac* flour either by washing with water or by precipitating with ethanol to increase the glucomannan content to greater than 90% or higher.

Rapidly dissolvable *konjac* flour is produced by grinding the refined *konjac* flour into finer particles either in the presence of ethanol or in a frozen state. All of these products are commercially available.

The term "glucommanna-rich flour" as used herein collectively refers to refined *konjac* flour, purified glucomannan flour and rapidly dissolvable *konjac* flour.

According to the present invention, the starting glucomannan-rich flour is dissolved in water to make a solution. Since the glucomannan solution is very viscous, its concentration needs to be less than 5%, preferably from 0.5 to 1.5% by weight. The solution is then mixed with ethanol, preferably by adding the solution gradually to ethanol with stirring whereupon glucomannan precipitates as fibrous particles.

Since glucomannan is not soluble in ethanol or an aqueous ethanolic mixture containing more than 30% of ethanol, the ratio of ethanol to the glucomannan solution must be at least 3:7.

In the next step, the precipitated glucomannan particles are reacted with an alkali to produce a water-insoluble, thermally irreversible hydrogel. The reaction may be carried out by adding an alkali solution to the water-ethanol mixture containing the precipitated glucomannan. Any alkali such as sodium hydroxide, sodium carbonate, potassium hydroxide or potassium carbonate may be used. A saturated lime water is preferable as is common practice in the production of edible *konjac*. Different from edible *konjac*, glucomannan gels while retaining fibrous particulate form. This makes easier the separation of gel from the liquid.

The gel particles are then separated from the liquid in a centrifuge, for example, and washed with an aqueous ethanol at least once. If necessary, the washing solution may contain a non-toxic organic acid such as acetic or citric acid to neutralize the excess of alkali.

The gel particles thus separated are thoroughly dried to remove the majority of water in a conventional apparatus, preferably in a hot air dryer at about 105° C. The dried gel particles are then milled and sieved to obtain a final product having a size as desired ranging between 10 and 500 microns. For use in hygienic and cosmetic preparations, a particle size from 50 to 500 microns is preferable.

EXAMPLES

The following examples are intended to further illustrate the present invention without limiting thereto. All parts and percents therein are by weight unless otherwise indicated.

Example 1

One kg of commercial refined *konjac* flour was added to 100 L of water. After stirring for 30 minutes, the mixture was allowed to stand for 3 hours at room temperature whereupon the flour dissolved completely to make a viscous solution. The solution was then added portionwise while stirring to 80 L of 95% aqueous ethanol and allowed to stand whereupon glucomannan precipitated out as fibrous particles. After adding 1 L of saturated lime water with gentle stirring, the mixture was allowed to stand and centrifuged to separate the resulting gel particles from the liquid. The gel particles were then resuspended in 5 L of 50% aqueous ethanol and centrifuged again to collect the gel particle. This washing process was repeated several times until the washing solution is substantially free of alkaline substances. The washed wet cake was dried in a hot air dryer at 105° C. for two days, milled and sieved to obtain dry glucomannan particles having an average particle size of about 100 microns.

Example 2

This example illustrates typical hygienic and cosmetic formulations containing the gel particles produced in Example 1.

| Material | Parts by weight |
| --- | --- |
| 1. Cleansing foam | |
| Detergent | 40.0 |
| Emolient | 5.0 |
| Preservative | 0.3 |
| Moisturizer | 15.0 |
| Glucomannan gel particles | 2.0 |
| Perfume | 0.1 |
| Purified water | q.s. |
| Total | 100.0 |
| 2. Toothpaste | |
| Calcium hydrogen phosphate | 40.0 |
| Glycerine | 17.35 |
| CMC sodium | 1.75 |
| Saccharin sodium | 0.20 |
| Butyl p-hydroxybenzoate | 0.20 |
| Sodium laurylsulfate | 2.00 |
| Glucomannan gel particles | 2.00 |
| Lauroylsarcosine sodium | 2.00 |
| Perfume | 1.15 |
| Purified water | q.s. |
| Total | 100.00 |
| 3. Cleansing powder | |
| Glucomannan gel particles | 2.0 |
| Cinnamon extract | 1.5 |
| Aluminum chloride hydroxide | 3.0 |
| 1-Menthol | 0.05 |
| Kaolin | 20.0 |
| Lactose | 0.5 |
| CMC sodium | 0.1 |
| Butyl p-hydroxybenzoate | 0.1 |
| Perfume | q.s. |
| Talc | q.s. |
| Total | 100.00 |
| 4. Face cleansing liquid preparation | |
| Glucomannan gel particles | 3.0 |
| Stearic acid | 5.0 |
| Myristic acid | 12.0 |
| Lauric acid | 7.0 |
| Glycerine fatty acid monoester | 3.0 |
| Sodium acetylglutamate | 20.0 |
| Anhydrous caffeine | 0.03 |
| Glycerine | 10.0 |
| CMC sodium | 0.1 |
| Perfume | q.s. |
| Purified water | q.s. |
| Total | 100.0 |
| 5. Shampoo | |
| Glucomannan gel particles | 5.0 |
| Coconut fatty acid diethanolamide | 5.0 |
| Sodium polyoxyethylenelauryl sulfate | 15.0 |
| Sodium polyoxyethylenealkylsulfosuccinate | 7.0 |
| Coconut fatty acid propyldimethylaminoacetic betaine | 10.0 |
| Anhydrous caffeine | 0.1 |
| CMC sodium | 0.2 |
| Perfume | q.s. |
| Purified water | q.s. |
| Total | 100.0 |
| 6. Rinser liquid | |
| Glucomannan gel particles | 2.0 |
| Stearyl trimethylammonium chloride | 2.0 |
| Cetyl alcohol | 2.0 |
| Silicone oil | 3.0 |
| Polyoxyethylene(10)oleyl ether | 1.0 |
| Glycerine | 5.0 |
| Polyethyleneglycol | 0.05 |
| Butyl p-hydroxybenzoate | 0.05 |
| Perfume | q.s. |
| Purified water | q.s. |
| Total | 100.0 |

I claim:

1. A process for preparing a particulate glucomannan gel comprising the steps of:
    a) dissolving a glucomannan-rich flour in water to make a solution;
    b) mixing the solution with ethanol to precipitate glucomannan by gradually adding the solution to the ethanol while stirring;
    c) adding an alkali to the resulting mixture to transform the precipitated glucomannan particles into water-insoluble, irreversible hydrogel particles;
    d) separating the glucomannan hydrogel particles from the liquid;

e) drying the separated hydrogel particles; and f) milling and sieving the dried gel particles to an average particle size of 10 to 500 microns.

2. A process according to claim 1, wherein said glucomannan-rich flour has a glucomannan content of at least about 80% by weight.

3. A process according to claim 2, wherein said glucomannan-rich flour is refined *konjac* flour or purified glucomannan flour.

4. A process according to claim 1, wherein said glucomannan flour is dissolved in step a) to a concentration less than 5% by weight.

5. A process according to claim 4, wherein said concentration is from 0.5 to 1.5% by weight.

6. A process according to claim 1, wherein said solution is added portionwise to ethanol in step b) such that the final concentration of ethanol in the mixture remains 30% or higher.

7. A process according to claim 1 further comprising between steps d) and e) the step of washing the separated hydrogel particles with a water-ethanol mixture at least once.

8. A process according to claim 7, wherein the water-ethanol mixture contains a non-toxic organic acid to neutralize excessive alkali.

9. A process according to claim 1, wherein said drying step e) is carried out at a temperature of about 105° C.

10. A process according to claim 1, wherein the dried glucomannan gel particles are divided in step f) to an average particle size from 50 to 500 microns.

11. A process for preparing a particulate glucomannan gel according to claim 1, wherein in mixing step b) the ratio of ethanol to the glucomannan solution is at least 3:7.

12. A process for preparing a particulate glucomannan gel according to claim 1, wherein in alkali in step c) is sodium hydroxide, sodium carbonate, potassium hydroxide or potassium carbonate.

13. A process for preparing a particulate glucomannan gel according to claim 1, wherein in alkali in step c) is a saturated lime water.

14. A process according to claim 8, wherein the non-toxic organic acid is acetic acid or citric acid.

15. A process for preparing a particulate glucomannan gel comprising the steps of:

a) dissolving a glucomannan-rich flour in water to make a solution;

b) adding the solution of step (a) portionwise to ethanol while stirring such that the final concentration of ethanol in the mixture remains 30% or higher to precipitate glucomannan;

c) adding an alkali to the resulting mixture to transform the precipitated glucomannan particles into water-insoluble, irreversible hydrogel particles;

d) separating the glucomannan hydrogel particles from the liquid;

e) drying the separated hydrogel particles; and f) milling and sieving the dried gel particles to an average particle size of 10 to 500 microns.

16. A particulate glucomannan gel produced by the process of claim 1.

17. A hygienic or cosmetic composition comprising a deposit-cleaning amount of the particulate glucomannan gel of claim 16 and a hygienically or cosmetically acceptable carrier.

18. A hygienic or cosmetic composition of claim 17 in the form of a cleansing foam, a toothpaste, a cleansing powder, a face cleansing liquid composition, a shampoo, or a rinser liquid composition.

* * * * *